(12) United States Patent
Lee et al.

(10) Patent No.: US 8,911,482 B2
(45) Date of Patent: Dec. 16, 2014

(54) INTERLOCKING BONE PLATE SYSTEM

(75) Inventors: Cheng-Hung Lee, Taichung (TW);
Chih-Han Chang, Tainan (TW);
Chih-Kun Hsiao, Kaohsiung (TW);
Kui-Chou Huang, Taichung (TW);
Chih-Hui Chen, Taichung (TW)

(73) Assignee: Taichung Veterans General Hospital, Taichung (TW)

( * ) Notice: Subject to any disclaimer, the term of this patent is extended or adjusted under 35 U.S.C. 154(b) by 409 days.

(21) Appl. No.: 13/418,668

(22) Filed: Mar. 13, 2012

(65) Prior Publication Data
US 2013/0096630 A1 Apr. 18, 2013

(30) Foreign Application Priority Data

Oct. 17, 2011 (TW) .............................. 100137556 A

(51) Int. Cl.
*A61B 17/80* (2006.01)
*A61B 17/58* (2006.01)
*A61B 17/72* (2006.01)
*A61B 17/86* (2006.01)

(52) U.S. Cl.
CPC ......... *A61B 17/7283* (2013.01); *A61B 17/8057* (2013.01); *A61B 17/8061* (2013.01); *A61B 17/8605* (2013.01); *A61B 17/8625* (2013.01)
USPC ................ 606/286; 606/62; 606/64; 606/291

(58) Field of Classification Search
USPC .......................... 606/62, 64, 70, 71, 286, 291
See application file for complete search history.

(56) References Cited

U.S. PATENT DOCUMENTS

| | | | | |
|---|---|---|---|---|
| 2,614,559 A * | 10/1952 | Livingston | ...................... | 606/64 |
| 3,670,724 A * | 6/1972 | Bosacco | ........................ | 606/64 |
| 3,709,218 A * | 1/1973 | Halloran | ........................ | 606/64 |
| 4,790,302 A * | 12/1988 | Colwill et al. | .................. | 606/62 |
| 7,425,231 B2 * | 9/2008 | Carolan et al. | .................... | 95/54 |
| 8,157,803 B1 * | 4/2012 | Zirkle et al. | .................... | 606/64 |
| 8,486,072 B2 * | 7/2013 | Haininger | ...................... | 606/64 |
| 8,734,448 B2 * | 5/2014 | Thakkar | ......................... | 606/64 |
| 2003/0135212 A1 * | 7/2003 | Chow | ............................. | 606/64 |
| 2006/0235400 A1 * | 10/2006 | Schneider | ...................... | 606/69 |
| 2009/0177240 A1 * | 7/2009 | Perez | .......................... | 606/86 R |

* cited by examiner

*Primary Examiner* — Nicholas Woodall
(74) *Attorney, Agent, or Firm* — Muncy, Geissler, Olds & Lowe, P.C.

(57) ABSTRACT

An interlocking bone plate system includes an outer bone plate for being arranged outside a broken bone, an inner bone plate for being installed inside the medullary cavity of the broken bone, and screws for being inserted through and engaged with the outer bone plate and the broken bone and then engaged with the inner bone plate so as to interlock the out and inner bone plates together. The inner bone plate provides an added support in addition to the support provided by the outer bone plate, enhancing the structural strength of the whole bone fixation structure and lowering the risk of failed surgery.

13 Claims, 4 Drawing Sheets

INTERLOCKING BONE PLATE SYSTEM

BACKGROUND OF THE INVENTION

1. Field of the Invention

The present invention relates to orthopedic instruments and more particularly, to an interlocking bone plate system for rigidly affixing bone segments.

2. Description of the Related Art

Conventionally, a bone plate and screws are used in surgery for fixation of a comminuted or osteoporotic fracture. By means of the engagement force between the screws and the bone and the friction force between the bone plate and the bone, the bone plate is affixed to the surface of the bone at one side. This fixation method is not stable due to the fact that when the load from the patient during a movement of the patient is greater than the friction force between the bone plate and the surface of the bone, the bone plate may be forced to display, biasing the screws. Further, if the bone plate is not closely matched in configuration with the bone, or if the screws are fastened excessively tight or the bone bears an excessive load, bone repositioning after surgery may be destructed.

Due to the aforesaid drawbacks of conventional surgery, a new locking plate is created for healing a broken bone. A locking plate of this design has an inner thread in each screw hole thereof for engagement with an outer thread around the periphery of the head of each screw. Thus, when a locking plate is locked to a broken bone by screws, the locking plate is not kept in direct contact with the surface of the broken bone, minimizing bone contact surface area, avoiding periosteal compression, facilitating quick bone healing and enhancing structural stability.

However, the biodynamic effect of the fixation of the aforesaid new locking plate is still obscure. Further, a locking plate system of this design is quite expensive and requires a specifically designed surgical implement during surgery. Further, if the bone receives an excessive muscle tension or load after surgery, the fixation cannot sustain inverse deformation of the bone, leading to surgical failure.

SUMMARY OF THE INVENTION

The present invention has been accomplished under the circumstances in view. It is the main object of the present invention to provide an interlocking bone plate system for healing a broken bone, which provides a highly stable fixation structure.

To achieve this object of the present invention, an interlocking bone plate system is adapted for fixation of a fracture of a bone comprising a diaphysis, two epiphysises at two distal ends thereof, two metaphysises respectively connected between the diaphysis and the two epiphysises, an outer bone wall and a medullary cavity surrounded by the outer bone wall. The interlocking bone plate system comprises an outer bone plate attached to the bone adjacent to a predetermined area of an outer surface of the bone and comprising at least one first through hole, an inner bone plate set in the medullary cavity of the bone corresponding to the outer bone plate and comprising at least one second through hole corresponding to the at least one first through hole of the outer bone plate, and at least one screw for locking the outer bone plate and the inner bone plate to the bone. Each screw comprises a head for engaging in one the first through hole, and a shank engageable through the outer bone wall of the bone into one the second through hole. Thus, the inner bone plate gives an added support, enhancing the structural strength and lowering the risk of failed surgery.

Other advantages and features of the present invention will be fully understood by reference to the following specification in conjunction with the accompanying drawings, in which like reference signs denote like components of structure.

DETAILED DESCRIPTION OF THE INVENTION

By ways of the following examples in conjunction with the annexed drawings, the technical contents and features of the present invention will be fully understood.

Figure 2:
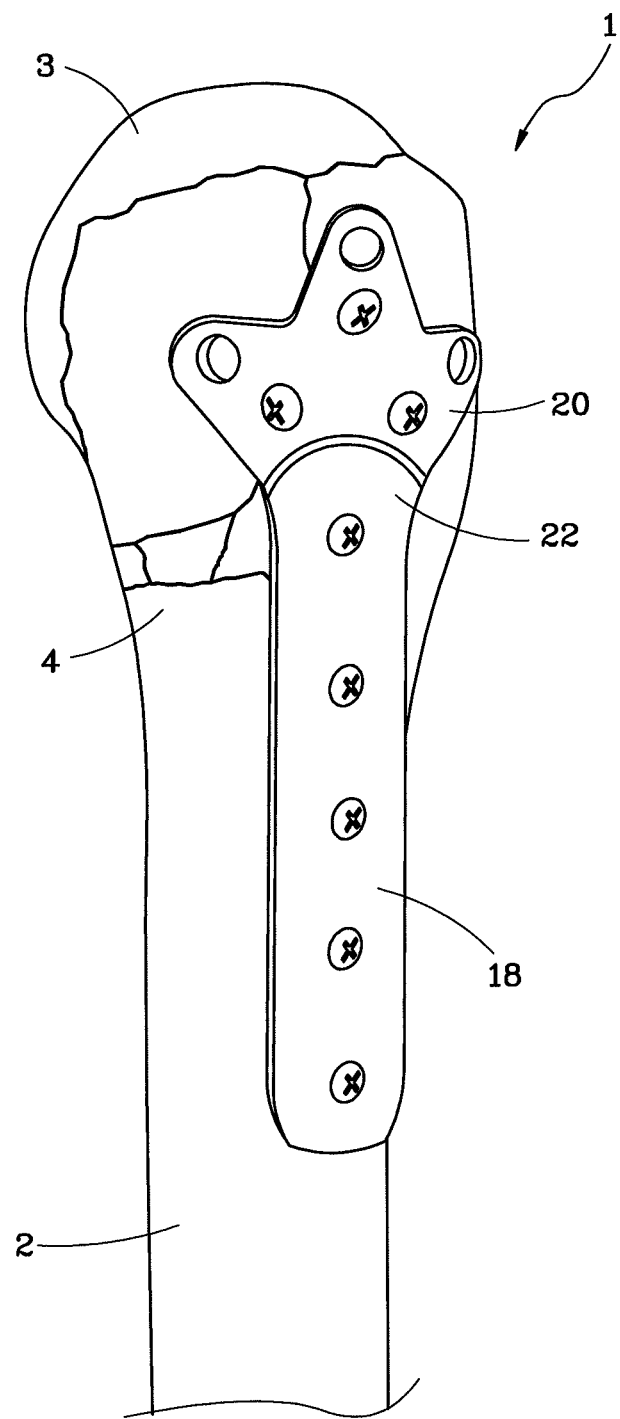
FIG. 2 is an elevational view of the first embodiment of the present invention, illustrating the interlocking bone plate system affixed to a bone.
Figure 3:
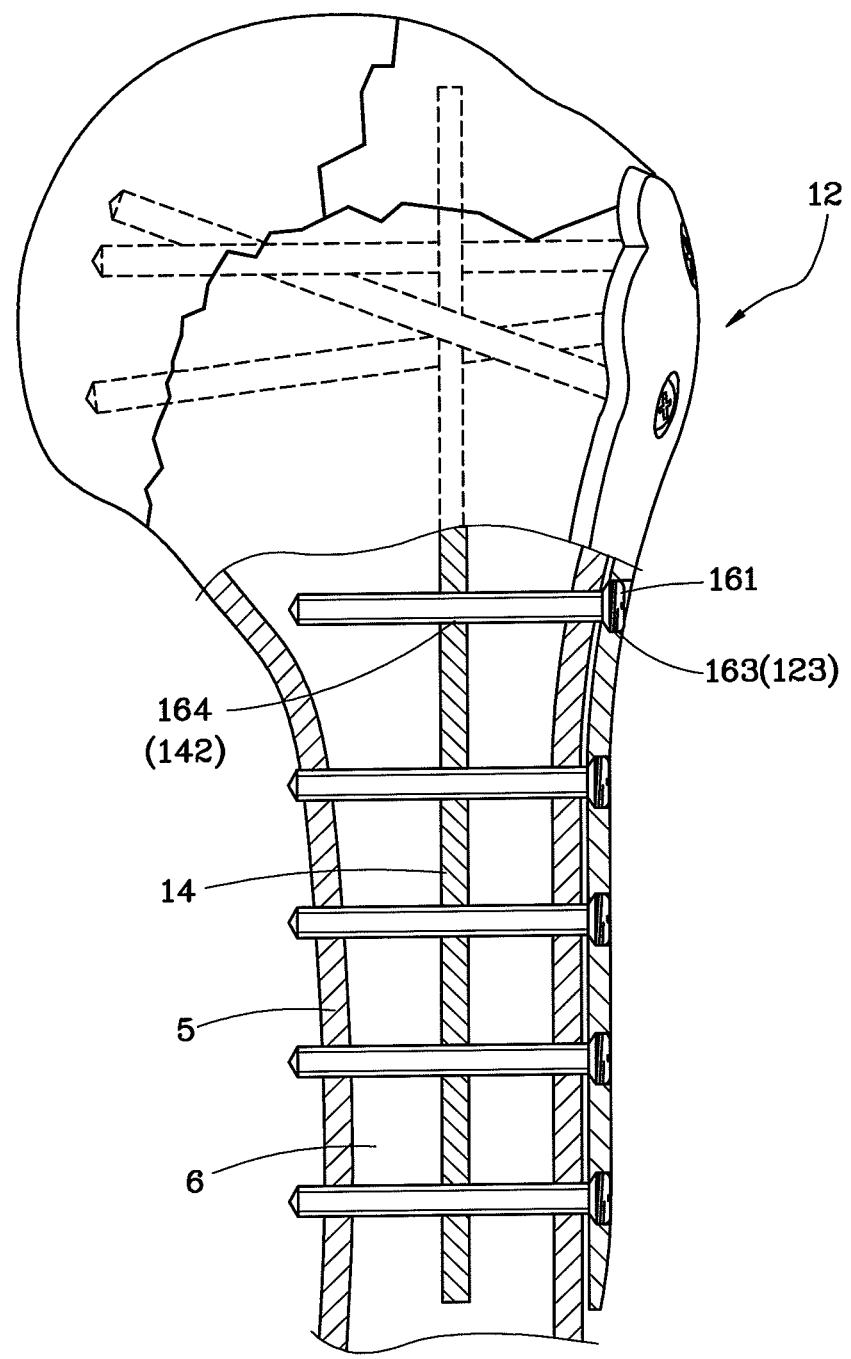
FIG. 3 is a schematic side view, partially in section, of the first embodiment of the present invention, illustrating the interlocking bone plate system affixed to the bone.

An interlocking bone plate system 10 is shown for healing a broken bone of a patient, more particularly, for fixation of a comminuted or osteoporotic fracture. As shown in FIG. 2 and FIG. 3, the structure of a bone 1 is symmetric. In the drawings, only one end of the bone 1 is shown for explanation. As illustrated, the bone 1 mainly comprises a diaphysis 2, two epiphysises 3 at the two distal ends thereof, two metaphysises 4 respectively connected between the diaphysis 2 and the two epiphysises 3, a bone wall 5, and a medullary cavity 6 surrounded by the bone wall 5. In this embodiment, the interlocking bone plate system 10 is affixed to one end of the bone 1, comprising an outer bone plate 12, an inner bone plate 14 and a plurality of screws 16.

Figure 1:
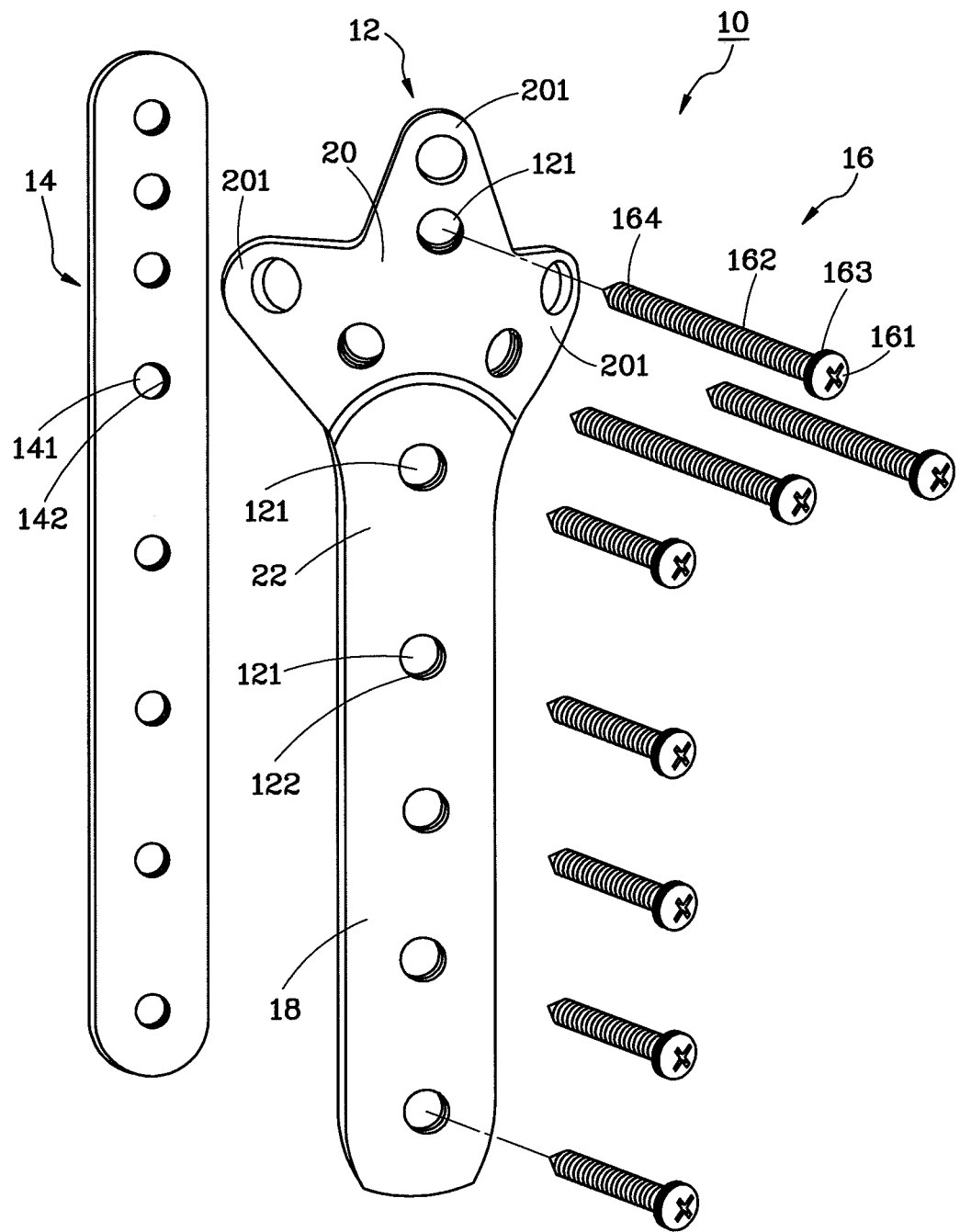
FIG. 1 is an exploded view of an interlocking bone plate system in accordance with a first embodiment of the present invention.

As shown in FIGS. 1-3, the outer bone plate 12 is arranged at a location outside the bone 1, and configured subject to the configuration of the bone 1. The outer bone plate 12 is kept in proximity to a predetermined area of the outer surface of the bone 1 at a predetermined distance, comprising a plurality of first through holes 121 and a first inner thread 122 in each of the first through holes 121. Specifically speaking, the outer bone plate 12 defines a diaphysis portion 18, an epiphysis portion 20 and a metaphysis portion 22. The diaphysis portion 18 is shaped like an elongated bar, having at least one first through hole 121 provided thereon. In this first embodiment, as shown in FIG. 1, four first through holes 121 are spacedly arranged on the diaphysis portion 18 in a line. The epiphysis portion 20 comprises a forked structure consisting of three protruding lugs 201, and at least one first through hole 121. In this first embodiment, as shown in FIG. 1, one first through hole 121 is located on one of the three protruding lugs 201. The metaphysis portion 22 is located between the diaphysis portion 18 and the epiphysis portion 20 and integrally joined with the diaphysis portion 18 and the epiphysis portion 20. The metaphysis portion 22 has at least one first through hole 121 provided thereon. In this first embodiment, as shown in FIG. 1, one first through hole 121 is provided on the metaphysis portion 22.

Referring to FIGS. 1 and 3 again, the inner bone plate 14 is shaped like an elongated bar and mounted inside the medullary cavity 6 of the bone 1 corresponding in location to the outer bone plate 12. The length of the inner bone plate 14 is slightly greater than that of the outer bone plate 12 so that one end of the inner bone plate 14 can be kept in proximity to one epiphysis 3 of the bone 1 in the medullary cavity 6. The inner bone plate 14 comprises at least one second through hole 141 and a second inner thread 142 in each second through hole 141. In this first embodiment, totally eight second through holes 141 are provided on the inner bone plate 14.

Each of the screws 16 comprises a head 161, a shank 162, a first outer thread 163 extending around the periphery of the head 161, and a second outer thread 164 extending around the periphery of the shank 162. As shown in FIG. 3, the screws 16 are respectively inserted through the outer bone plate 12, the bone 1 and the inner bone plate 14. The heads 161 of the screws 16 are respectively set in the first through holes 121. By means of threading the respective first outer threads 163 into the respective first inner threads 122, the heads 161 of the screws 16 are respectively engaged into the first through holes 121. By means of the respective second outer threads 164, the shanks 162 of the screws 16 are driven through and engaged with the bone wall 5 of the bone 1. Further, by means of threading the respective second outer threads 164 into the respective second inner threads 142, the shanks 162 of the screws 16 are respectively engaged into the second through holes 141. Thus, the outer bone plate 12 outside the bone 1 and the inner bone plate 14 in the medullary cavity 6 are spacedly and interconnectedly secured together.

Based on the aforesaid technical features, the interlocking bone plate system of the present invention comprises an inner bone plate set in the medullary cavity for fixation with an outer bone plate outside the bone to be healed. Through the dual support design, the outer and inner bone plates of the interlocking bone plate system effectively share the tension force received by the bone after surgery. When the bone receives a great load pressure, the inner bone plate can additionally provide a support against the compression force, enhancing the structural strength of the fixation. This design of interlocking bone plate system has a structural strength five times greater than similar conventional bone plate systems. Thus, the interlocking bone plate system of the present invention can bear a high load, preventing inverse deformation of the bone and lowering the risk of failed surgery. Further, performing a surgical operation using the interlocking bone plate system of the present invention does not require any other particular surgical implements.

Figure 4:
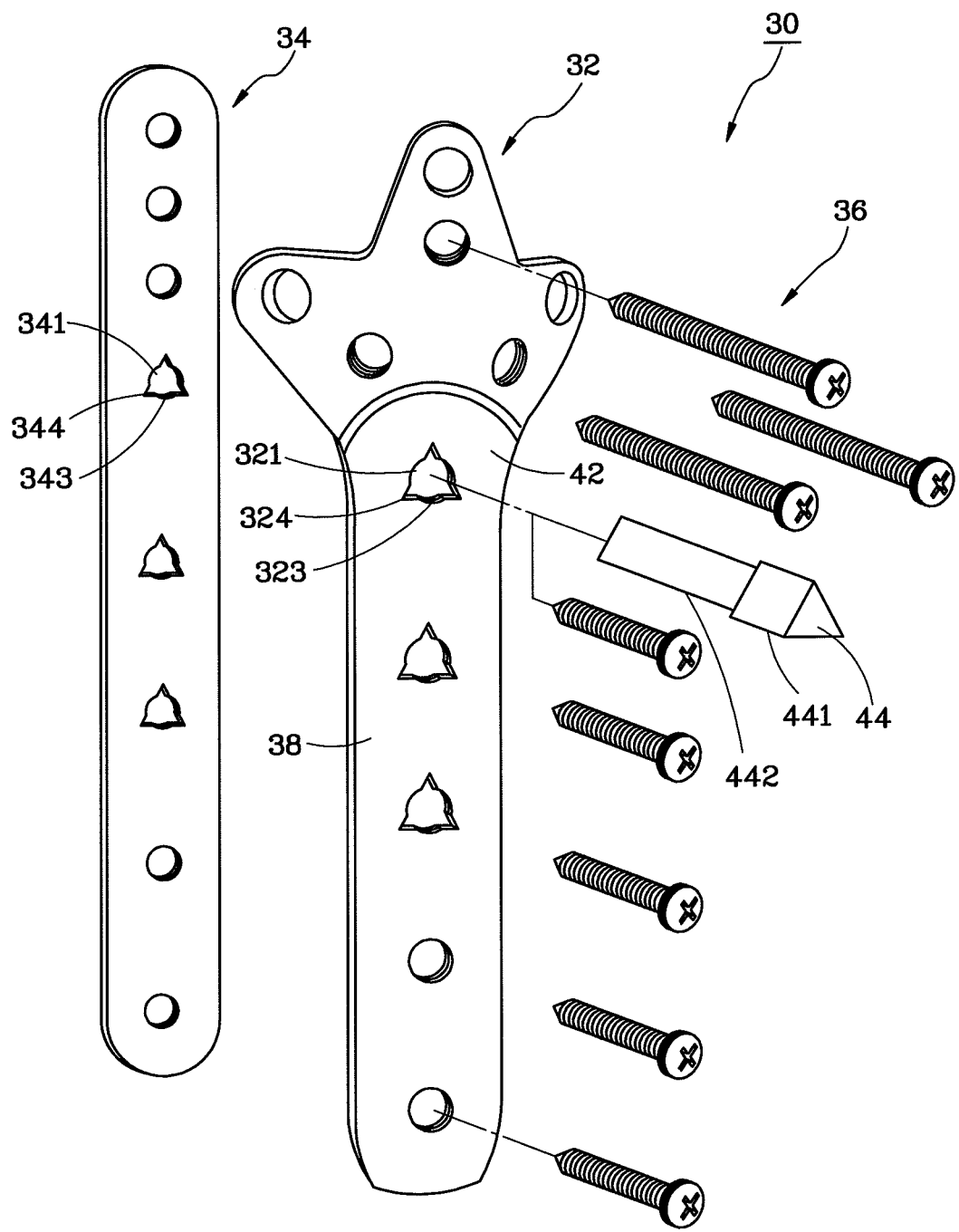
FIG. 4 is an exploded view of an interlocking bone plate system in accordance with a second embodiment of the present invention.

FIG. 4 illustrates an interlocking bone plate system 30 in accordance with a second embodiment of the present invention. This second embodiment is substantially similar to the aforesaid first embodiment with the exception that the first through hole 321 at the metaphysis portion 42 of the outer bone plate 32 and the first two first through holes 321 at the diaphysis portion 38 of the outer bone plate 32 adjacent to the metaphysis portion 42 each define a first peripheral edge 323 and three first positioning portions 324 located on the first peripheral edge 323; the three second through holes 341 of the inner bone plate 34 corresponding to the first through hole 321 at the metaphysis portion 42 of the outer bone plate 32 and the first two first through holes 321 at the diaphysis portion 38 of the outer bone plate 32 adjacent to the metaphysis portion 42 each define a second peripheral edge 343 and three second positioning portions 344 located on the second peripheral edge 343. The interlocking bone plate system 30 further comprises an anchor member 44, which comprises three first anchoring portions 441 and three second anchoring portions 442.

Each of the first anchoring portions 441 corresponds to one respective first positioning portion 324 of one of the respective first through hole 321. Each of the second anchoring portions 442 corresponds to one respective second positioning portion 344 of one of the respective second through hole 341. As shown in FIG. 4, the first anchoring portions 441 and the second anchoring portions 442 are shaped like a block, specifically a sharp-edged block, thus, the anchor member 44 exhibits a triangular cross section. The first positioning portion 324 and the second positioning portions 344 are notches, specifically are sharp notches. The anchor member 44 is detachably insertable through one first through hole 321 and the corresponding second through hole 341. Thus, the first through hole 321 at the metaphysis portion 42 of the outer bone plate 32 and the first two first through holes 321 at the diaphysis portion 38 of the outer bone plate 32 adjacent to the metaphysis portion 42 and the corresponding second through holes 341 allow insertion of respective screws 36 and selectively insertion of the anchor member 44. When the inner bone plate 34 is set in the medullary cavity 6 of the bone 1, the anchor member 44 can be inserted through one first through hole 324 and the broken zone of the bone into the corresponding second through hole 341 to temporarily secure the inner bone plate 34 and the outer bone plate 32 in a proper angle and position, and then respective screws 36 can be fastened to the outer bone plate 32 and the inner bone plate 34 to fixedly fasten the outer bone plate 32 and the inner bone plate 34 to the bone, and then the anchor member 44 can be removed from the outer bone plate 32 and the inner bone plate 34 for insertion of one screw 36 as a substitute. Thus, the interlocking bone plate system 30 is accurately and conveniently affixed to the fracture area of the bone.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. An interlocking bone plate system for fixation of a fracture of a bone including a diaphysis, an epiphysis, a metaphysis between said diaphysis and said epiphysis, a bone wall and a medullary cavity surrounded by said bone wall, the interlocking bone plate system comprising:

an outer bone plate for being arranged outside said bone adjacent to an outer surface of said bone, said outer bone plate comprising at least one first through hole;

an inner bone plate for being installed inside said medullary cavity of said bone corresponding to said outer bone plate, said inner bone plate comprising at least one second through hole; and at least one screw comprising a head for being engaged with said at least one first through hole, and a shank for being inserted through and engaged with said bone wall of said bone and engaged with said at least one second through hole; such that said outer bone plate and said inner bone plate are spacedly interlockable;

wherein said first through hole of said outer bone plate defines a first peripheral edge and a first positioning portion located on said first peripheral edge; said second through hole of said inner bone plate defines a second peripheral edge and a second positioning portion located on said second peripheral edge corresponding to the first positioning portion of said first through hole.

2. The interlocking bone plate system as claimed in claim 1, wherein said outer bone plate comprises a diaphysis portion, an epiphysis portion and a metaphysis portion, which are capable of corresponding to said diaphysis, said epiphysis and said metaphysis of said bone respectively.

3. The interlocking bone plate system as claimed in claim 2, wherein said at least one first through hole is provided on at least one of said diaphysis portion, said epiphysis portion and said metaphysis portion.

4. The interlocking bone plate system as claimed in claim 1, further comprising an anchor member detachably insertable through said first through hole and said second through hole, said anchor member comprising a first anchoring portion engageable into said first positioning portion and a second anchoring portion engageable into said second positioning portion.

5. The interlocking bone plate system as claimed in claim 4, wherein the first positioning portion of said first through hole and the second positioning portion of said second through hole are notches; said first anchoring portion and said second anchoring portion are blocks.

6. The interlocking bone plate system as claimed in claim 1, wherein said first through hole comprises a first inner thread; said screw further comprises a first outer thread extending around a periphery of the head for being threaded into the first inner thread of said first through hole.

7. The interlocking bone plate system as claimed in claim 1, wherein said second through hole comprises a second inner thread; said screw further comprises a second outer thread extending around a periphery of the shank for being threaded into the second inner thread of said second through hole.

8. An interlocking bone plate system, comprising:
an outer bone plate comprising a first through hole;
an inner bone plate comprising a second through hole; and
a screw comprising a head engaged with said first through hole, and a shank engaged with said second through hole, such that said outer bone plate and said inner bone plate are spacedly interlocked;
wherein said first through hole of said outer bone plate defines a first peripheral edge and a first positioning portion located on said first peripheral edge; said second through hole of said inner bone plate defines a second peripheral edge and a second positioning portion located on said second peripheral edge corresponding to the first positioning portion of said first through hole.

9. The interlocking bone plate system as claimed in claim 8, wherein said outer bone plate comprises a diaphysis portion, an epiphysis portion and a metaphysis portion, and the first through hole is provided on one of said diaphysis portion, said epiphysis portion and said metaphysis portion.

10. The interlocking bone plate system as claimed in claim 9, further comprising an anchor member detachably insertable through said first through hole and said second through hole, said anchor member comprising a first anchoring portion engageable into said first positioning portion and a second anchoring portion engageable into said second positioning portion.

11. The interlocking bone plate system as claimed in claim 10, wherein the first positioning portion of said first through hole and the second positioning portion of said second through hole are notches; said first anchoring portion and said second anchoring portion are blocks.

12. The interlocking bone plate system as claimed in claim 8, wherein said first through hole comprises a first inner thread; said screw further comprises a first outer thread extending around a periphery of the head and threaded into the first inner thread of said first through hole.

13. The interlocking bone plate system as claimed in claim 8, wherein said second through hole comprises a second inner thread; said screw further comprises a second outer thread extending around a periphery of the shank and threaded into the second inner thread of said second through hole.

* * * * *